United States Patent [19]

Ekinaka et al.

[11] 4,173,392
[45] Nov. 6, 1979

[54] GLASS FIBER LIGHT GUIDE AND METHOD OF MAKING THE SAME

[75] Inventors: Michael H. Ekinaka, Irvine; Richard B. MacAnally, Altadena, both of Calif.

[73] Assignee: American Hospital Supply Corporation, Evanston, Ill.

[21] Appl. No.: 817,152

[22] Filed: Jul. 20, 1977

[51] Int. Cl.$^2$ .............................................. G02B 5/17
[52] U.S. Cl. .................................. 350/96.26; 264/1; 350/96.25; 350/320
[58] Field of Search .............. 350/96 B, 96 BC, 96.24, 350/96.25, 96.26, 320; 264/1, 300, 319

[56] References Cited

U.S. PATENT DOCUMENTS

| | | | |
|---|---|---|---|
| 2,992,956 | 7/1961 | Bazinet | 350/96 B X |
| 3,216,807 | 11/1965 | Woodcock | 350/96 BC X |
| 3,261,351 | 7/1966 | Wallace | 350/96 B X |
| 3,434,775 | 3/1969 | Gosselin | 350/96 BC |
| 3,799,150 | 3/1974 | Bonnet | 350/96 BC UX |
| 3,941,121 | 3/1976 | Olinger et al. | 350/96 BC X |

*Primary Examiner*—John K. Corbin
*Assistant Examiner*—John D. Lee
*Attorney, Agent, or Firm*—Tilton, Fallon, Lungmus & Chestnut

[57] ABSTRACT

A low-friction, abrasion-resistant, non-shedding glass fiber light guide and its method of construction. The light guide is particularly suited for endoscopic use in conjunction with other elements which may contact the light guide but must not either damage the guide or be damaged by it. The light guide comprises an elongated bundle of generally parallel glass fibers embedded in a hardened resin matrix, the bundle being ensheathed by a pair of thin protective layers disposed on opposite sides thereof, converging along a pair of side edges, and secured in place by the resinous matrix material. The method for making the light guide involves the steps of lining a mold cavity with a thin film, introducing the glass fibers and a hardenable liquid potting compound into the cavity, covering the exposed fibers and compound with a second film, rearranging the fibers and compound to establish the desired cross-sectional configuration, and then heating the mold and its contents until the resin is cured. In the disclosed embodiment, the desired cross-sectional configuration is of crescent shape. The light guide is also disclosed in combination with other coacting elements of an endoscope assembly.

22 Claims, 6 Drawing Figures

GLASS FIBER LIGHT GUIDE AND METHOD OF MAKING THE SAME

BACKGROUND AND SUMMARY

In co-pending co-owned application Ser. No. 795,405, filed May 9, 1977, there is disclosed a modular rod lens assembly particularly suited for use in endoscopes. The assembly takes the form of a thin metal outer tube containing a series of small rod lens modules dimensioned and arranged to transmit an optical image from one end of the assembly to the other. Enclosed within the same tube is a bundle of light-transmitting glass fibers. In use, the glass fiber bundle transmits light through the tube to illuminate that portion of the body undergoing examination, the lens system then returning the image of the illuminated area to the eye of the surgeon or other person utilizing the instrument.

Such an assembly must be manufactured to extremely high standards of precision and cleanliness if the assembly is to perform its microscope functions efficiently and effectively. Because of the frangibility of glass fibers, difficulties have been encountered in the past in potting such fibers to form a bundle of precise dimensions without damaging the fibers and producing debris either from the fibers themselves or from the potting material. Also, because of the hardness of such fibers, contact between the bundle and the surfaces of other elements, such as the inside surface of the endoscope tube or barrel, may result in abrasion, damage, and the generation of particulate matter. Should any such particulate matter enter the spaces between the opposing end faces of successive rod lenses, the optical performance of the microscope might be seriously impaired, particularly because in a rod lens system, unlike camera systems, the faces of the lenses often lie in or near the image planes. Therefore, any particulate matter on the end faces of the rod lenses might appear in the field of view when the completed assembly is put to use.

An important aspect of this invention lies in the discovery that the difficulties of fabricating a potted glass fiber bundle, as well as the problems arising in the assembly and use of such a bundle in conjunction with the other elements of an endoscope, may be greatly reduced if the bundle is cast or molded between a pair of films which not only simplify removal of the bundle from the mold but which become part of the final light guide to reduce friction, improve abrasion resistance, and virtually eliminate all problems of shedding and debris development. Specifically, the films protect the glass fibers against damage from other elements, protect such other elements (such as the rod lens modules and the endoscope barrel) against abrasive contact by such fibers, reduce frictional resistance when the light guide and other elements are assembled to form the endoscope, and virtually eliminate shedding and debris formation which might impair the effectiveness of the final instrument.

Briefly, the method comprises the steps of lining the cavity of a mold with a thin flexible film of plastic or other suitable material, introducing a multiplicity of generally parallel glass fibers and a liquid potting resin into the lined cavity, covering the exposed fibers and resin with a second film, then introducing an insert element into the cavity to reform the assemblage of films, resin, and fibers into a predetermined cross-sectional configuration, and then allowing the potting compound to pass into its hardened state to form a dimensionally stable structure in which the films are secured in place to form a protective sheath.

The completed light guide is ideally crescent-shaped in cross section although other configurations might be suitable. In the final endoscope assembly, the convex curvature of the crescent-shaped light guide engages the inside surface of the endoscope barrel while the concave curvature contacts the rod lens modules. During assembly of such components, the protective films provide smooth abrasion-resistant non-shedding surfaces, thereby eliminating or greatly reducing the possibility of damage to the waveguide itself or to the other elements of the instrument. Furthermore, where the instrument is capable of limited flexure, the abrasion-resistant cladding continues to perform its important functions in protecting the parts and preventing debris formation during such occasional flexure and throughout the useful life of the instrument.

Other advantages and objects of the invention will become apparent from the specification and drawings.

DRAWINGS

DETAILED DESCRIPTION

Figure 6:
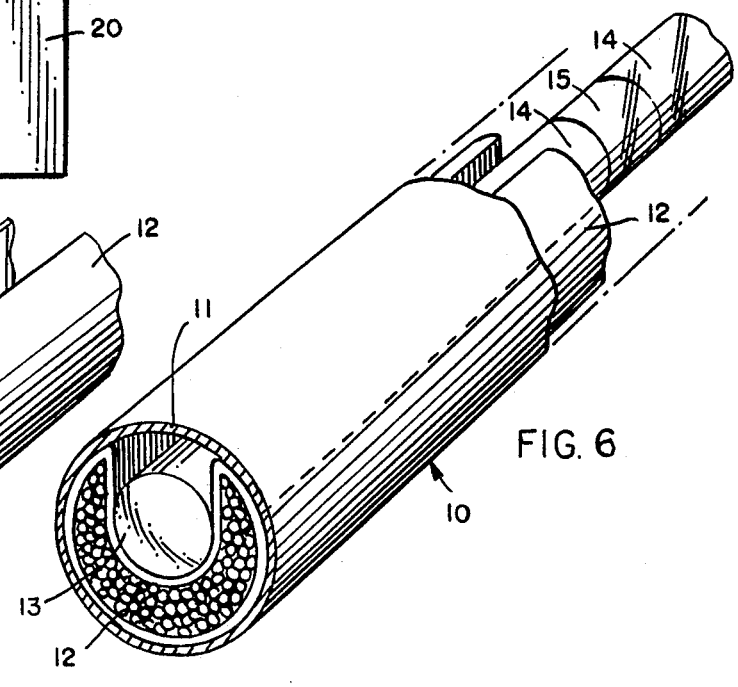
FIG. 6 is a perspective view showing the light guide assembled within an endoscope, the barrel of the endoscope and the light guide being cut away to illustrate the relationship of parts.

Referring to the drawings, FIG. 6 illustrates an endoscope 10 having a tubular barrel 11 formed of stainless steel or other rigid, durable material. Within the barrel is a light guide 12 and an image-transmitting optical assembly 13. In the form illustrated, the assembly 13 comprises a series of glass rod lenses 14 separated by spacer rings or collars 15. The entire structure is illustrated in greatly enlarged form. While the dimensions may vary depending on the intended use of the instrument, the outside diameter of tube or barrel 11 would not be expected to greatly exceed 0.16 of an inch if the instrument is designed for endoscopic use. On that basis, the inside diameter of the tube 11, and the outside diameter of light guide 12, would not be expected to exceed approximately 0.14 of an inch.

While other configurations might be utilized, the crescent shape of the light guide 12 is particularly desirable because of the effective utilization of space about the rod lens assembly. The outside convex surface of the light guide contacts the inside surface of the barrel, and the concave inside surface of the light guide receives and supports the lens assembly 13.

Figure 5:
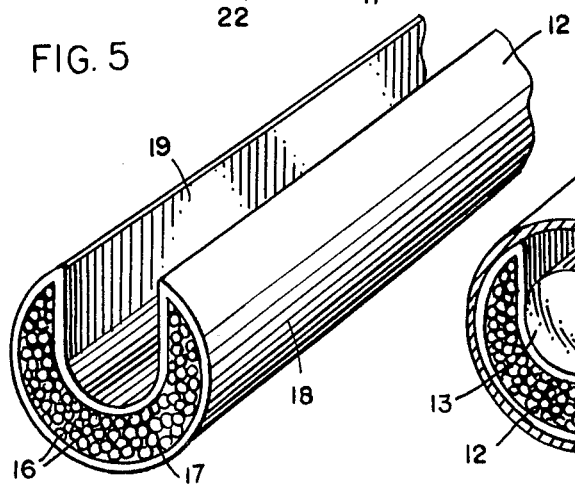
FIG. 5 is a perspective view illustrating the completed light guide.

From FIG. 5, it will be seen that the light guide is composed of a multiplicity of glass fibers 16 is disposed in parallel relation and embedded in a matrix 17 composed of a suitable potting compound. A thermosetting or heat-curable material such as epoxy has been found particularly effective; however, other materials capable of passing from a liquid state into a hardened state, either with or without the addition of heat, may also be used. The outer convex surface of the glass-epoxy bundle is covered with a protective outer layer 18 and the inner concave surface is covered with a protective inner layer 19. Both layers may be composed of thin films of polyglycol terephthalate or other tough, hard, and abrasion-resistant materials. While plastic materials are believed particularly effective, it is to be understood that metal foil might conceivably be used. In any event, the thickness of the film or covering is relatively thin, within the general range of 0.001 to 0.0001 of an inch, the optimum thickness for endoscopic use being thought to be about 0.00025 of an inch. Where the potting compound is thermosetting, the material selected for the protective layers must have a melting temperature well above the treatment temperature of the matrix material.

Figure 1:
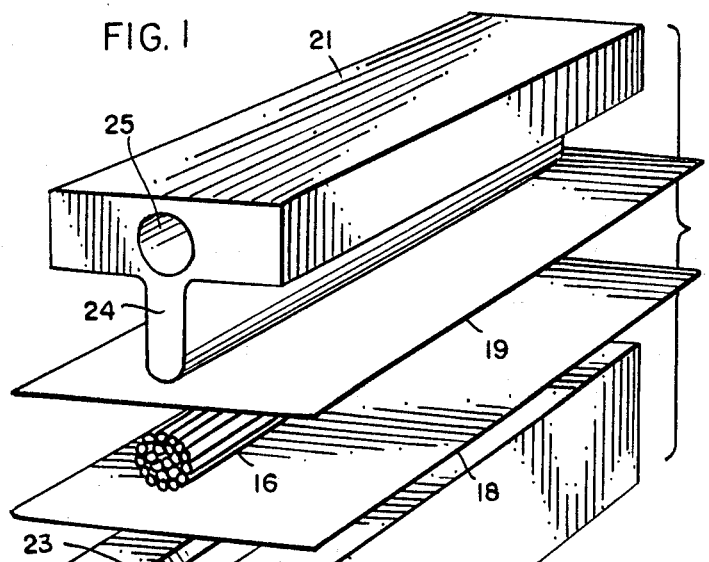
FIG. 1 is an exploded perspective view schematically illustrating the main components and their relationship for carrying out the method of this invention.

FIG. 1 is a schematic view which illustrates the relationship of the glass fibers 16 (the potting material is omitted) and films 18 and 19 in relation to a mold 20 and an insert element 21. The mold 20, shown as a two-piece mold, has a cavity 22 with a longitudinal opening 23 serving as an entrance to the cavity. The cavity is elongated and, except for that portion merging with the entrance, is generally cylindrical in configuration.

The insert element 21 includes a longitudinal projection or rib 24 which is dimensioned to be received within the entrance of the mold cavity and which is rounded at its lower end portion to serve as a male molding element, the cavity-providing assembly 20 serving as the female mold. An opening 25 is provided for installation of a cylindrical electrical resistance heater (not shown) where a thermosetting potting material is selected.

Figure 3:
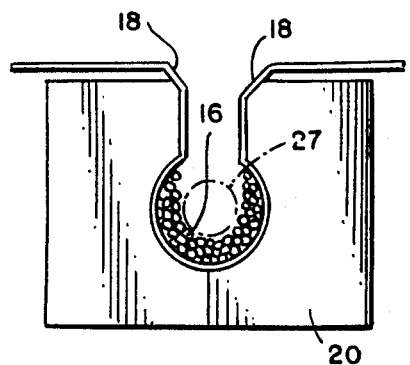
FIG. 3 is an end elevational view similar to FIG. 2 but showing the cavity after the potting compound and glass fibers have been introduced.
Figure 2:
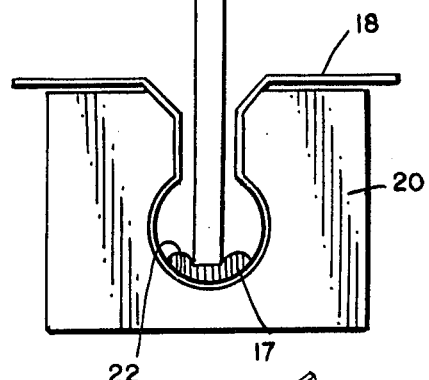
FIG. 2 is an end elevational view showing the introduction of potting compound into a lined mold cavity during an early stage of the method.
Figure 4:
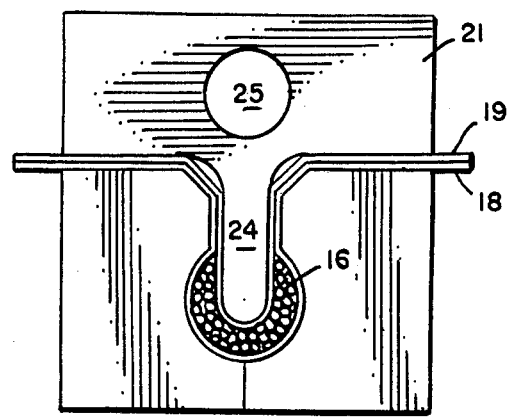
FIG. 4 is an end elevational view depicting a subsequent step in the method.

Major steps of the operative procedure are depicted in FIGS. 2-4. After placing film 18 within mold cavity 22 to line that cavity and its entrance (the width of the film being substantially greater than the dimension of the cross-sectional contour of the cavity and its entrance), a liquid potting agent 17 is introduced into the lined cavity by means of a syringe 26, or by any other suitable means (FIG. 2). A selected quantity of glass fibers are then introduced into the lined cavity and are brought into contact with the liquid potting agent (FIG. 3). While it is believed preferable to place the liquid potting compound 17 into the lined mold cavity in advance of introducing the glass fibers, these steps may be reversed or, in some cases, may be performed in successive partial stages in order to insure proper intermixing of the fibers and potting compound.

Thereafter, the second film 19 is urged into the mold to cover the exposed fibers and liquid potting material. Again, the width of the film 19 is substantially greater than necessary to cover the exposed fibers and material, the excess film material extending upwardly out of the neck of the mold cavity and overlying the excess portions of the first film 18. The projection 24 of insert element 21 is then inserted into the entrance of the mold and into the mold cavity to cause rearrangement of the fibers and potting material and to cause the assemblage to assume its final cross-sectional configuration (FIG. 4). The potting material is then allowed to harden to form a sold matrix which not only bonds the fibers together into a solid bundle but which also securely holds the inner and outer film layers in place. Where the potting material is thermosetting, heat may be applied to the mold and its contents, and to insert 21, to cure the potting material.

Prior to introducing the second film 19 and the insert element 21, the arrangement of fibers 16 may be altered to "pre-form" the mixture of fibers and potting compound into the arcuate configuration depicted in FIG. 3. The pre-forming step may be carried out using any suitable tool; in the illustration given, a rod 27 with rounded ends is moved axially through the mold cavity to displace the fibers and bonding agent. If desired, the rod diameter may be slightly larger than the diameter of the cavity so that the rod cannot escape upwardly through the neck of the cavity but must move axially to rearrange the fibers and matrix material.

It is to be noted that some rearrangement of the fibers and matrix necessarily occurs when the second film 19 and insert element 24 are introduced, even if the pre-forming step is carried out, because the potting compound is in a fluid or semi-fluid state as the element 24 is inserted into the mold. The importance of the pre-forming step is that the extent of fiber displacement is reduced in the later stage when the insert element is introduced into the space or recess left by the pre-forming tool (rod), thereby eliminating problems of fiber damage that might otherwise occur at that stage.

Once the matrix material has hardened, insert 21 is removed, the sections of mold 20 are separated, and the excess film material is trimmed from the upper edges of the light guide. It is believed apparent that the films 18 and 19 not only become a permanent part of the finished product, thereby overcoming the problems and disadvantages of prior constructions, but also serve as release elements to line and protect the mold and insert during the fabrication process.

While in the foregoing we have disclosed an emodiment of the invention in considerable detail for purposes of illustration, it will be understood by those skilled in the art that many of these details may be varied without departing from the spirit and scope of the invention.

We claim:

1. A method for making a low-friction abrasion-resistant glass fiber light guide, comprising the steps of lining the cavity of a mold with a thin flexible film; introducing into the lined cavity a multiplicity of generally parallel glass fibers and a liquid potting material capable of passing into a hardened state; covering the exposed fibers and potting material with a second thin flexible film; introducing an insert element into the cavity to reform the assemblage of films, potting material, and fibers into a final predetermined cross-sectional configuration; then allowing said potting material to pass into its hardened state to embed and fix said fibers against relative movement, and withdrawing said insert element.

2. The method of claim 1 in which there is an additional step of pre-forming the fibers and liquid potting material into an approximation of said final cross-sectional configuration in advance of the step of covering said fibers and potting material with said second film.

3. The method of claim 2 in which said pre-forming step is performed by moving a rod through said mold cavity along the length of said fibers to displace said fibers and potting materially laterally and to create a recess for the introduction of said second film and said insert element.

4. The method of claim 1 in which said potting material is thermosetting; said last-mentioned step including heating the mold and its contents until said potting material has hardened.

5. The method of claim 4 in which said potting compound is an epoxy resin.

6. The method of claim 1 in which said films are formed of plastic material.

7. The method of claim 6 in which said films are formed of polyglycol terephthalate.

8. The method of claim 1 in which there is the further step of removing the assemblage from the mold after the potting material has hardened, said films providing a permanent protective covering for the potted glass fibers therein.

9. The method of claim 8 in which there is the further step of trimming excess material from the edges of the films after the assemblage is removed from the mold.

10. The method of claim 1 in which said films are of a thickness within the range of 0.001 to 0.0001 of an inch.

11. The method of claim 10 in which said films are of a thickness of approximately 0.00025 of an inch.

12. The method of claim 1 in which the cavity of said mold is arcuate in cross section and said insert element presents a rounded surface having a cross section of substantially smaller radius than the curvature of said arcuate mold cavity, whereby, the light guide formed by said method is generally crescent-shaped in cross section.

13. The method of claim 1 in which said cavity, films, and insert element are all elongated and are of substantially the same length as said parallel glass fibers.

14. A low-friction, abrasion-resistant, nonshedding glass fiber light guide comprising an elongated bundle of generally parallel glass fibers embedded in a hardened matrix material; said bundle being generally crescent-shaped in cross section; and a pair of thin flexible protective layers fixedly secured to the convex and concave surfaces of said bundle by said matrix material.

15. The light guide of claim 14 in which said thin protective layers are formed of plastic material and completely cover said convex and concave surfaces of said bundle.

16. The light guide of claim 15 in which said plastic layers are formed of polyglycol terephthalate.

17. The light guide of claim 15 in which said layers are coextensive with said convex and concave surfaces of said bundle.

18. The light guide of claim 14 in which said layers are formed of thin films of polyglycol terephthalate.

19. The light guide of claim 18 in which said films are of a thickness within the range of 0.001 to 0.0001 of an inch.

20. The light guide of claim 19 in which said films are of a thickness of approximately 0.00025 of an inch.

21. The light guide of claim 14 in which said matrix material is an epoxy resin.

22. The light guide of claim 14 in combination with a cylindrical endoscope barrel and an image-transmitting optical system, said endoscope barrel being tubular and having an inside surface in engagement with the convex outer surface of said light guide; said optical system being received by the concave surface of said light guide within said endoscope barrel.

* * * * *